(12) United States Patent
Eichhorn et al.

(10) Patent No.: US 6,818,010 B2
(45) Date of Patent: Nov. 16, 2004

(54) SUTURE ANCHOR SYSTEM FOR JOINING PIECES OF TISSUE AND INSTRUMENT FOR INSERTING AN ANCHOR IMPLANT

(75) Inventors: Juergen Eichhorn, Mitterfels/Scheibelsgrub (DE); Nicola Giordano, Villingen-Schwenningen (DE); Karl-Ernst Kienzle, Tuttlingen (DE); Gerhard Kirmse, Tuttlingen (DE)

(73) Assignee: Aesculap AG & Co. KG, Tuttlingen (DE)

(*) Notice: Subject to any disclaimer, the term of this patent is extended or adjusted under 35 U.S.C. 154(b) by 230 days.

(21) Appl. No.: 10/281,921

(22) Filed: Oct. 25, 2002

(65) Prior Publication Data

US 2003/0105489 A1 Jun. 5, 2003

Related U.S. Application Data

(63) Continuation of application No. PCT/EP01/04279, filed on Apr. 14, 2001.

(30) Foreign Application Priority Data

Apr. 29, 2000 (DE) .......................................... 100 21 122

(51) Int. Cl.[7] .............................................. A61B 17/04
(52) U.S. Cl. .......................... 606/232; 606/72; 606/73
(58) Field of Search ........................... 606/232, 72, 73, 606/103

(56) References Cited

U.S. PATENT DOCUMENTS

| | | | |
|---|---|---|---|
| 5,037,422 A | | 8/1991 | Hayhurst et al. |
| 5,059,206 A | | 10/1991 | Winters |
| 5,224,946 A | | 7/1993 | Hayhurst et al. |
| 5,236,445 A | | 8/1993 | Hayhurst et al. |
| 5,258,016 A | | 11/1993 | DiPoto et al. |
| 5,545,180 A | * | 8/1996 | Le et al. ..................... 606/232 |
| 5,575,819 A | | 11/1996 | Amis |
| 5,702,462 A | | 12/1997 | Oberlander |
| 5,730,744 A | | 3/1998 | Justin et al. |
| 5,733,307 A | * | 3/1998 | Dinsdale ..................... 606/232 |
| 5,782,866 A | * | 7/1998 | Wenstrom, Jr. ............. 606/232 |
| 5,843,084 A | | 12/1998 | Hart et al. |
| 5,891,168 A | | 4/1999 | Thal |
| RE36,289 E | * | 8/1999 | Le et al. ..................... 606/232 |
| 6,007,566 A | | 12/1999 | Wenstrom, Jr. |
| 6,508,830 B2 | * | 1/2003 | Steiner ....................... 606/232 |

FOREIGN PATENT DOCUMENTS

| | | |
|---|---|---|
| DE | 691 07 703 | 10/1995 |
| DE | 37 51 400 | 12/1995 |
| DE | 38 55 610 | 3/1997 |
| EP | 0 589 306 | 3/1994 |
| EP | 0 664 198 | 6/1999 |
| EP | 0 982 003 | 3/2000 |
| WO | 85/03857 | 9/1985 |

* cited by examiner

Primary Examiner—Glenn K. Dawson
Assistant Examiner—Darwin P Erezo
(74) Attorney, Agent, or Firm—Barry R. Lipsitz; Douglas M. McAllister

(57) ABSTRACT

In a suture anchor system for joining pieces of tissue, in particular, for repairing meniscal tears, comprising at least two arrow-shaped or pin-shaped anchor implants joined to one another by a flexible suture fastened to the anchor implants, in order to facilitate installation of the anchor implants, it is proposed that at least one of the anchor implants have a continuous longitudinal passageway for receiving a longitudinally displaceable core, that a suture guide for receiving a suture common to all anchor implants for longitudinal displacement in the suture guide be disposed on this anchor implant, that a clamping device for securing the suture in the suture guide be associated with the suture guide, and that the clamping device be inactive so long as the core is located inside the longitudinal passageway and only become active when the core is pulled out of the longitudinal passageway. An instrument for inserting such anchor implants is also described.

20 Claims, 4 Drawing Sheets

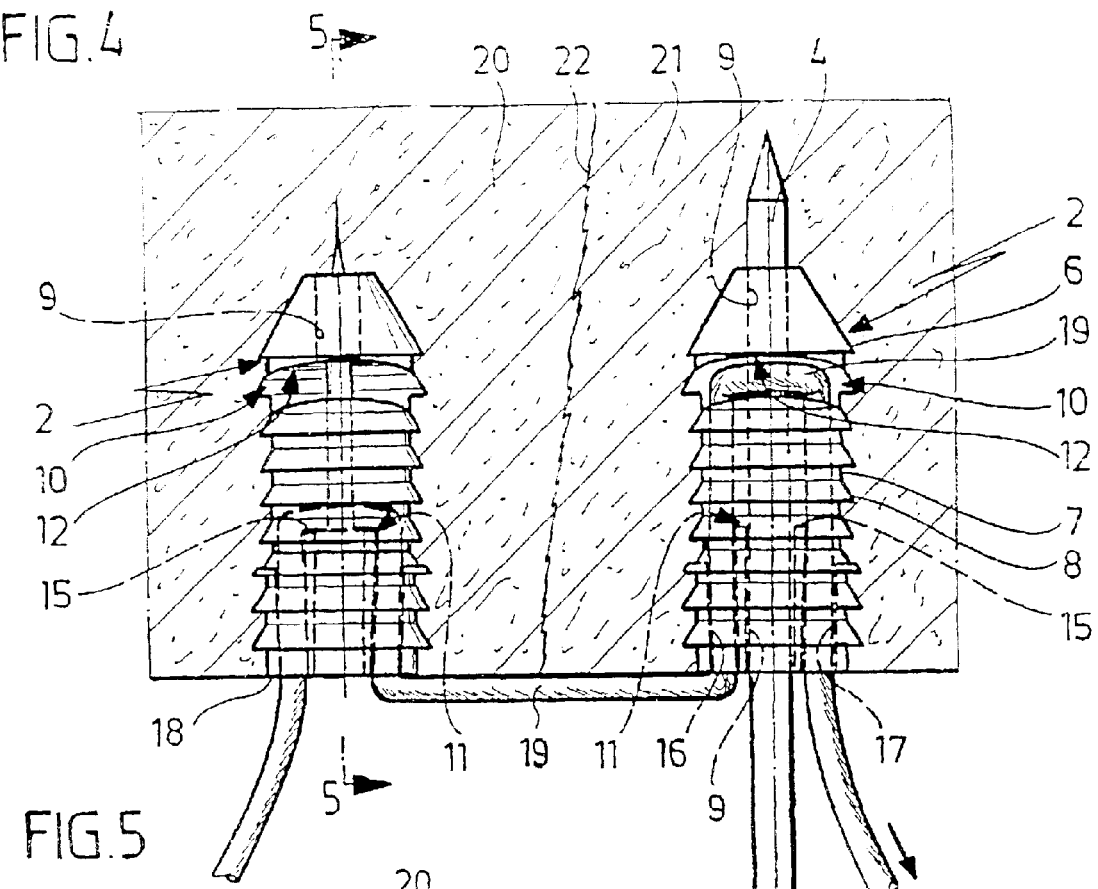
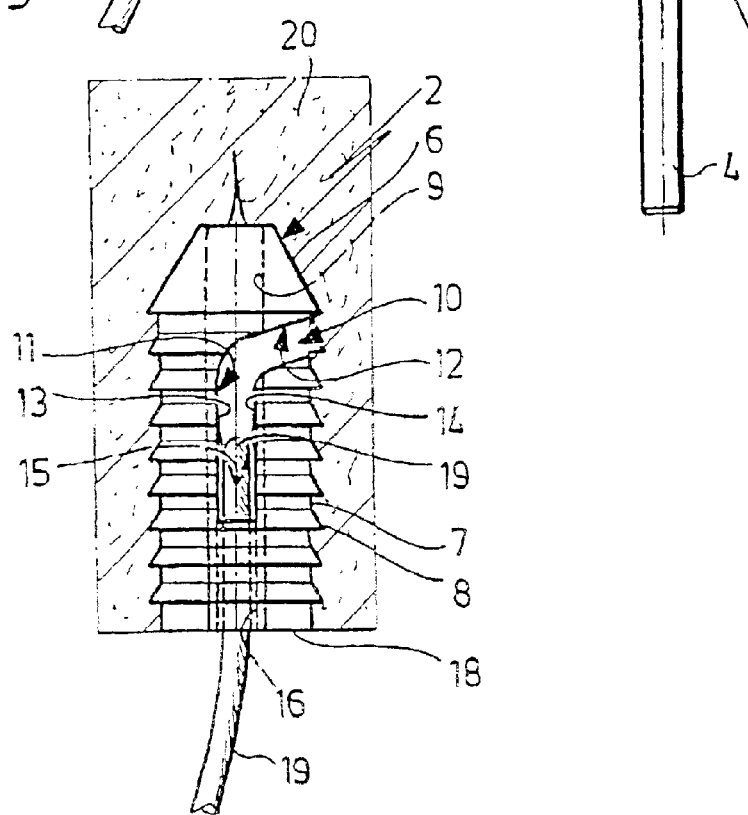

SUTURE ANCHOR SYSTEM FOR JOINING PIECES OF TISSUE AND INSTRUMENT FOR INSERTING AN ANCHOR IMPLANT

The present disclosure is a continuation application and relates to the subject matter disclosed in international application PCT/EP01/04279 of Apr. 14, 2001, which is incorporated herein by reference in its entirety and for all purposes.

BACKGROUND OF THE INVENTION

The invention relates to a suture anchor system for joining pieces of tissue, in particular, for repairing meniscal tears, comprising at least two arrow-shaped or pin-shaped anchor implants joined to one another by a flexible suture fastened to the anchor implants.

The invention further relates to an instrument for inserting such an anchor implant.

To join pieces of tissue, for example, the parts of a meniscus separated from one another by a tear, it is known to introduce into the pieces of tissue arrow-shaped anchor implants which by means of barbs or a barbed design are secured in the pieces of tissue against removal. These implants can directly join the pieces of tissue to be attached to one another by penetrating both pieces of tissue (WO 85/03857; U.S. Pat. No. 5,843,084) or two such arrow-shaped anchor implants are joined together by a flexible intermediate member so as to thereby bridge the junction (EP 0 589 306 A2; EP 0 664 198 B1).

Moreover, a suture anchor system is described in U.S. Pat. No. 5,702,462, in which dart-type anchor implants each have a suture securely attached thereto, and the sutures of various anchor implants are knotted together after insertion of the anchor implants into the tissue so that the pieces of tissue to be joined together are joined by the suture bridges. However, this procedure is relatively complicated as the suture ends of two respective anchor implants have to be knotted together, and, in addition, the knots form a thickening in the suture which may cause irritation of the tissue.

The object of the invention is to so design a generic suture anchor system that it can be installed in a particularly simple way and that, in particular, the formation of knots can be dispensed with.

SUMMARY OF THE INVENTION

This object is accomplished in a suture anchor system of the kind described at the outset, in accordance with the invention, in that at least one of the anchor implants has a continuous longitudinal passageway for receiving a longitudinally displaceable core, in that a suture guide for receiving a suture common to all anchor implants for longitudinal displacement in the suture guide is disposed on this anchor implant, in that a clamping device for securing the suture in the suture guide is associated with the suture guide, and in that the clamping device is inactive so long as the core is located inside the longitudinal passageway and only becomes active when the core is pulled out of the longitudinal passageway.

Thus, in contrast to known anchor implants, in the described suture anchor system at least two anchor implants are joined by a common suture, and on at least one of these anchor implants this suture is initially freely displaceable in a suture guide. Therefore, after insertion of the anchor implants in the tissue, the suture can be tensioned in the desired manner between the two anchor implants, and in this tensioned state the suture can then be secured on the anchor implants by the core being pulled out of the longitudinal passageway. Knot formation is no longer necessary, and yet it is possible to tension the suture joining the inserted anchor implants in the desired manner and to thereby secure the pieces of tissue to be joined in relation to one another.

In a first preferred embodiment provision is made for a first anchor implant to be securely fastened to the suture and for all other anchor implants to have a longitudinal passageway with a removable core and a suture guide with a clamping device. In this way, starting with a first anchor implant with a suture securely fastened thereto, any number of further anchor implants can first be displaceably threaded onto the same suture, but after insertion of the anchor implants, the suture can be tensioned between these anchor implants and secured. The suture anchor system may comprise only two anchor implants or a larger number of anchor implants.

The first anchor implant may also have a continuous longitudinal passageway for facilitating in a manner to be described hereinbelow installation of the anchor implant in the piece of tissue.

In another embodiment provision is made for all anchor implants to have a longitudinal passageway with a removable core and a suture guide with a clamping device, i.e., all anchor implants are initially freely displaceable on the suture and are only secured along the suture by removal of the core.

In particular, in such an embodiment it is of advantage for the one end of the suture to carry a stop element which upon tensioning of the suture bears against a piece of tissue and thereby prevents further drawing of the suture into the piece of tissue.

The core may be a ram-shaped part which is pulled out of the anchor implant to activate the clamping device. It is, however, particularly advantageous for the core to be a guide wire which is pushed through the anchor implant and lodged in the tissue, for it is then possible to advance the anchor implant along this guide wire into the desired position in the tissue. Thus, in this embodiment the guide wire both guides the anchor implant during insertion and activates the clamping device for the suture upon pulling out the guide wire.

The guide wire may also serve to position the pieces of tissue to be joined together relative to one another so that upon introducing the anchor implant, the pieces of tissue are secured in the desired position relative to one another. This can prevent these pieces of tissue from being joined in a crooked or overlapping manner.

It is favorable for the anchor implants to carry barbs or barb-like protrusions on their exterior surface so that anchor implants, once inserted, are secured in their position.

The anchor implant and/or the suture preferably consist of absorbable plastic material so these implants disintegrate in the body after completion of the healing process.

The core can render the clamping device active in different ways. For example, in the pushed-in state the core can displace a clamping element, for example, a flexible clamping tongue, movably disposed on the anchor implant, into a position in which this clamping element is unable to effectively block the suture. Once the core is pulled out of the anchor implant, this clamping element, which may, for example, be a barb, engages the suture and thereby prevents displacement of the suture relative to the anchor implant. These clamping elements may be barbs acting on one side or on both sides, i.e., barbs are provided for both directions of displacement of the suture, so the suture is secured against displacement in both directions after removal of the core.

In a particularly preferred embodiment provision is made for the suture guide to comprise a clamping section extending through the longitudinal passageway and a displacement section disposed adjacent the longitudinal passageway, for the core inserted in the anchor implant to block off the clamping section from the displacement section, and for the clamping device to be disposed in the clamping section, whereas the suture is freely displaceable in the displacement section.

In this construction, the clamping section is released by pulling out the core, the suture can move into the clamping section from the displacement section and is thereby secured against longitudinal displacement in the anchor implant.

The clamping device may have a multiplicity of projections or barbs for engaging the suture when the suture enters the clamping device and thereby securing the suture in the anchor implant.

In a particularly preferred embodiment provision is made for the clamping device to be a slot which tapers towards the bottom thereof, and into which the suture is placed and clamped between the side walls thereof when the suture is displaced towards the bottom of the slot.

It is of advantage for guides for the suture which are bent at an angle towards the bottom of the slot to adjoin the slot on both sides thereof. Once the suture is tensioned in these angled guides, it is automatically pulled into the slot, tensioned against the bottom thereof and thereby clamped in the slot.

These guides adjoining the slot may be in the form of channels open or closed at their sides, which extend at either side of the longitudinal passageway substantially parallel thereto in the anchor implant and at one end open into the bottom of the slot. In this way, both ends of the same suture exit the anchor implant on the same side thereof, and the suture thereby forms inside the anchor implant a U-shaped loop which is guided in the slot.

It is advantageous for the slot to extend diametrically through the anchor implant at least in the area of the clamping section.

The side walls of the slot may converge at an acute angle towards the bottom thereof. It is favorable for the side walls to have a concave curvature in cross section.

In a further preferred embodiment provision is made for the clamping section formed by the slot to continue at its end opposite the bottom thereof into the displacement section arranged outside the longitudinal passageway and likewise forming part of the slot, with the side walls of the slot in the displacement section being spaced at a distance from one another which is greater than the diameter of the suture.

The plane of the slot in the displacement section may be bent at an angle in relation to the plane of the slot in the clamping section, preferably at an angle of between 30° and 90°. It is favorable for the slot to be curved in the area of transition between the clamping section and the displacement section so that after removing the core and upon applying tension, the suture readily slides from the displacement section into the clamping section.

Provision may be made for the slot at the outer end of the displacement section to be open towards the outside at the circumferential surface of the anchor implant. This facilitates insertion of the suture into the anchor implant.

The following description of preferred embodiments of the invention serves in conjunction with the drawings to provide a more detailed explanation.

BRIEF DESCRIPTION OF THE DRAWINGS

FIG. 4 is a view similar to FIG. 2 after securing the suture joining the anchor implants to one anchor implant;

FIG. 5 is a sectional view along line 5—5 in FIG. 4; and

DETAILED DESCRIPTION OF THE INVENTION

Figure 1:
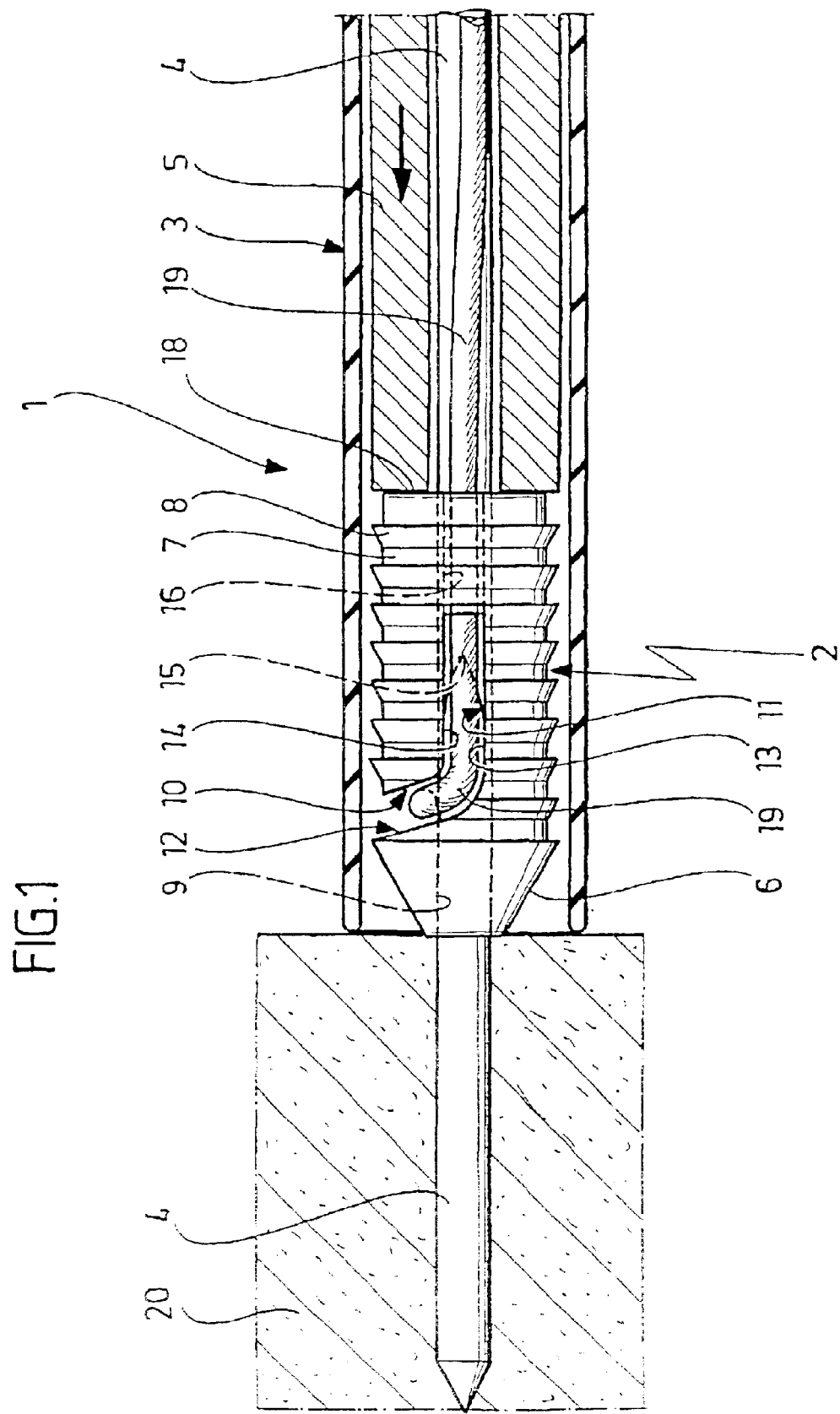
FIG. 1 is a longitudinal sectional view of the front part of an instrument for installing an anchor implant with an anchor implant positioned therein prior to introduction of the anchor implant into the tissue.

FIG. 1 shows an instrument 1 for inserting a circular cylindrical anchor implant 2 essentially comprising a flexible guide tube 3, a likewise flexible guide wire 4 disposed centrally within the guide tube 3 and projecting over the end of the guide tube 3, and a pusher member 5 mounted for longitudinal displacement inside the guide tube 3 and surrounding the guide wire 4. The guide wire 4 may likewise be mounted for longitudinal displacement in the guide tube 3. The pusher member and possibly the guide wire are displaced by means of handles, not shown in the drawings, at the opposite end of the guide tube 3. The external diameter of the guide tube 3 is selected such that it is also readily introducible into the interior of the body by means of conventional trocar sleeves. The external diameter of the guide tube 3 may, for example, be from 7 to 10 mm, preferably from 3 to 5 mm.

The guide tube of the insertion instrument may be introduced directly through an incision in the skin into a joint in which an anchor implant 2 is to be installed, for example, in the meniscus. With other indications, however, the guide tube 3 is introduced into the body in the described manner by a trocar sleeve.

The anchor implant 2 is a pin-shaped or arrow-shaped body having essentially the shape of a circular cylinder and consisting of an absorbable plastic material, preferably with a diameter of 2 to 3 mm, with a conical tip 6 and a multiplicity of barbed circumferential ribs 8 on its cylindrical outer surface 7. A central longitudinal passageway 9 penetrates the anchor implant 2, and this longitudinal passageway 9 receives the guide wire 4, i.e., from the open end of the guide tube 3 the anchor implant 2 is pushed into the interior of the guide tube 3 by means of the guide wire 4, so that the anchor implant 2 is fully accommodated in the guide tube 3, as shown in FIG. 1, when the pusher member 5 is in the retracted position.

In the central area thereof, the anchor implant 2 has a slot 10 penetrating it in a transverse direction. In a clamping section 11 thereof, the slot 10 extends diametrically through the anchor implant 2 parallel to the longitudinal direction of the anchor implant 2, and at its end facing the tip 6 the slot 10 continues into an outwardly open displacement section 12 oriented outwardly at an incline to the outer surface 7. The displacement section 12 is inclined at an angle of between 30° and 90° to the clamping section 11. In the area of transition between the clamping section 11 and the displacement section 12 the slot 10 is of curved configuration, i.e., the transition is not stepped, but steady.

The side walls 13 and 14 of the slot 10 converge at the bottom 15 of the slot 10 and meet there at an acute angle. In the adjoining wall areas, the side walls 13 and 14 are bent in slightly concave configuration (FIG. 5).

At opposite sides of the longitudinal passageway 9 there extend parallel thereto two closed guide channels 16, 17 which open into the bottom 15 of the slot 10 and at their other end exit from the rear side 18 located opposite the tip 6 of the anchor implant 2.

A flexible suture 19 placed in the anchor implant 2 enters the slot 10 through the one guide channel 16 and exits the slot 10 again through the other guide channel 17, with the result that the suture 19 forms a U-shaped loop in the anchor implant 2.

Figure 2:
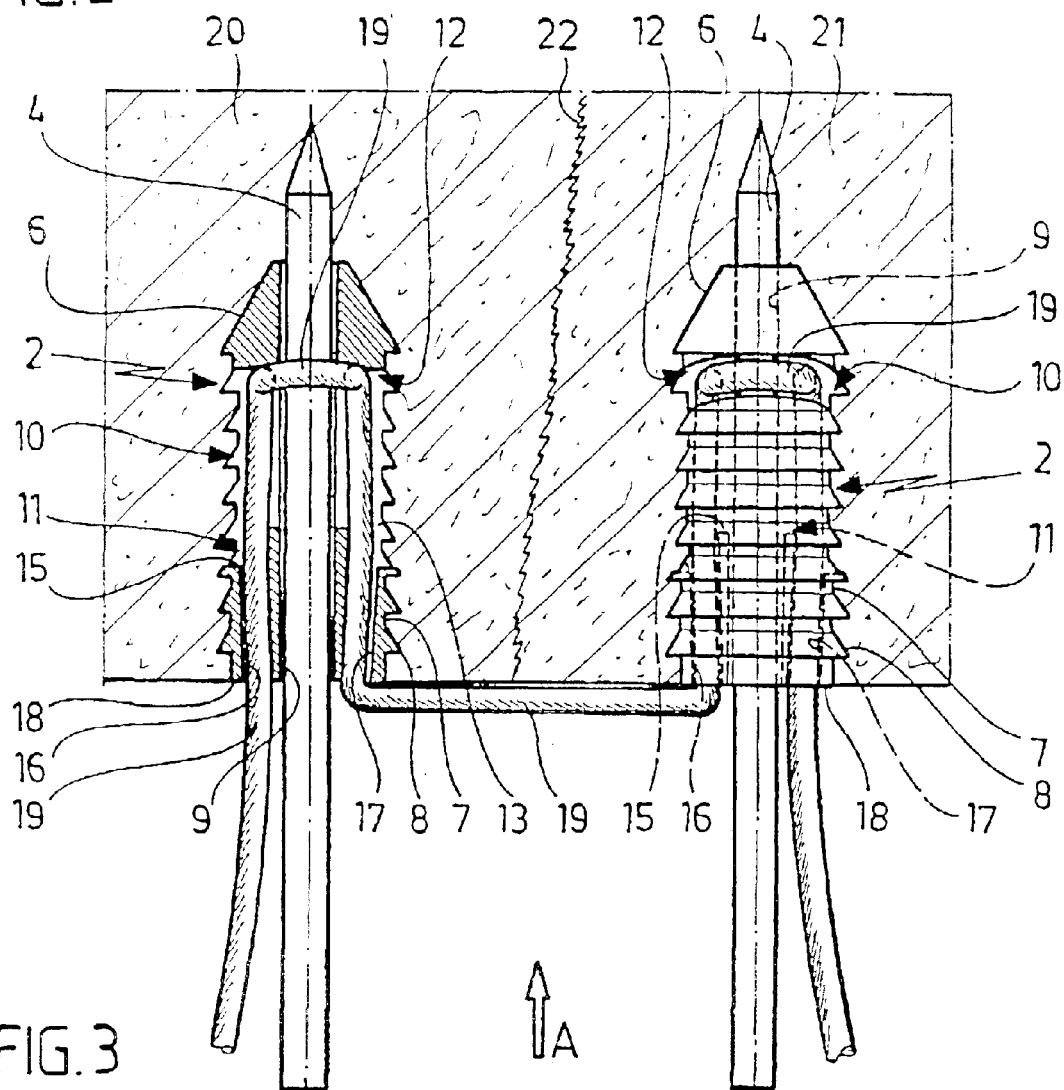
FIG. 2 is a sectional view through two pieces of tissue to be joined together with anchor implants positioned therein prior to tightening of the suture joining the anchor implants.
Figure 3:
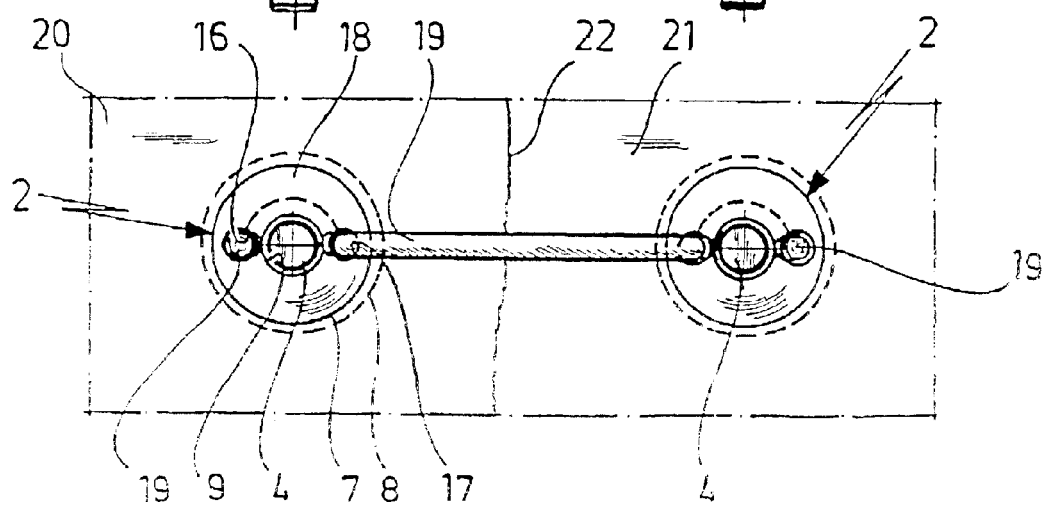
FIG. 3 is a view of the piece of tissue of FIG. 2 in the direction of arrow A in FIG. 2.

When the guide wire 4 is inserted in the longitudinal passageway 9 of the anchor implant 2, as shown, for example, in FIG. 1, the suture 19 is then unable to enter the clamping section 11 of the slot 10 as it is filled up by the guide wire 4, and the suture 19 then has to diverge into the displacement section 12 and in so doing engages in the shape of a semicircle the outer side of the guide wire 4 (FIGS. 1 and 2).

In the displacement section 12 the distance between the side walls 13 and 14 of the slot 10 is larger than the diameter of the suture 19 and the suture 19 is, therefore, freely displaceable in the displacement section 12.

When the guide wire 4 is removed from the longitudinal passageway 9, the suture 19 can slide into the clamping section 11. This occurs, in particular, when the suture 19 is tensioned at the two suture ends leading out of the anchor implant 2. The suture 19 thereby gets between the side walls 13 and 14 converging towards the bottom 15 and is clamped there, with the result that longitudinal displacement of the suture is no longer possible.

To install the described anchor implants 2, two such anchor implants 2 are inserted into two pieces of tissue 20, 21 which are to be joined together. To this end, an instrument 1 is applied to each piece of tissue 20, 21, i.e., a guide wire 4 is inserted, and an anchor implant 2 is pushed into the piece of tissue 20, 21 along the guide wire 4. The suture 19 extending in both anchor implants 2 is common to both anchor implants 2, i.e., this suture 19 bridges the junction 22 of the two pieces of tissue 20, 21.

So long as the guide wires 4 still remain in the pieces of tissue 20 and 21, the common suture 19 is freely displaceable in the longitudinal direction in both anchor implants 2.

Figure 6:
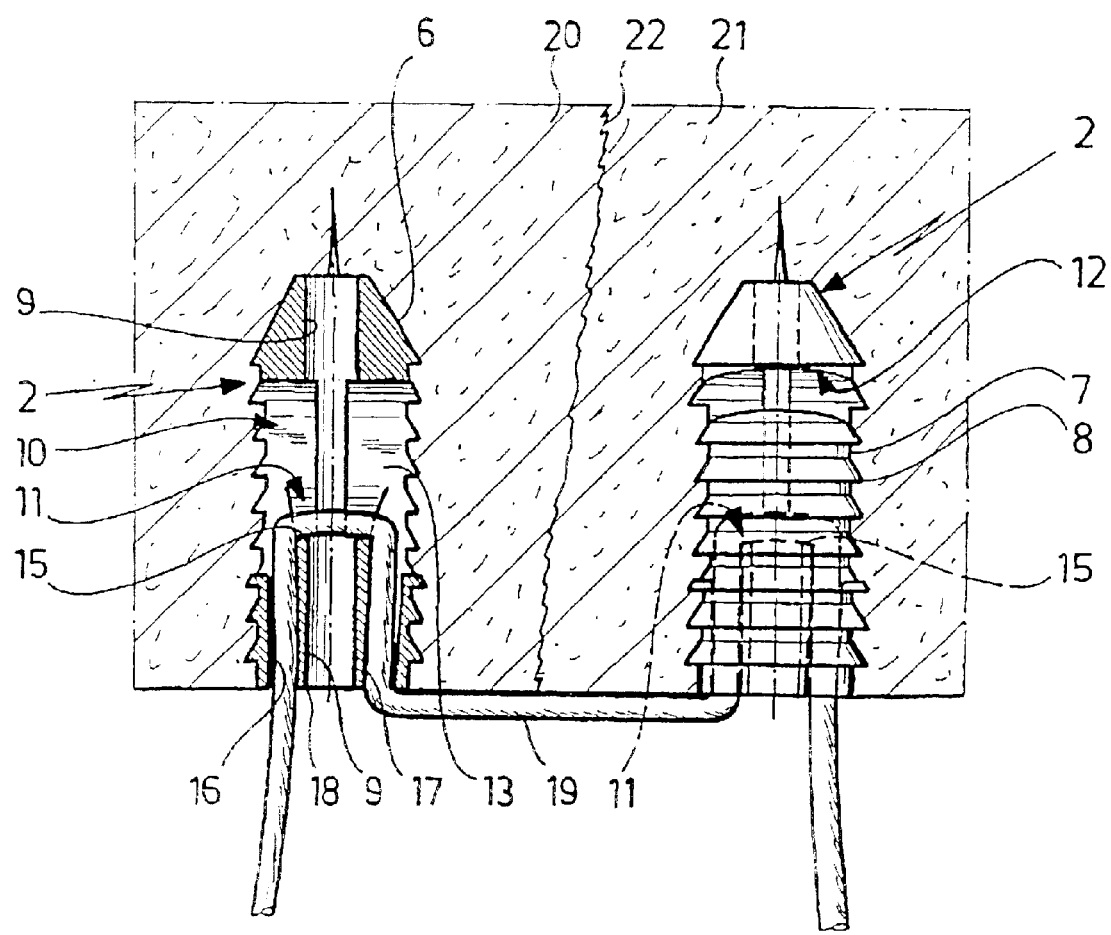
FIG. 6 is a view similar to FIG. 2 after securing the suture joining the anchor implants in both anchor implants.

By pulling out one guide wire 4 and by tightening the suture 19, the suture 19 in the anchor implant 2 out of which the guide wire 4 is pulled is displaced into the clamping section 11 and thereby fixed in the interior of the anchor implant 2 (left anchor implant in FIG. 4). It is now possible to displace the suture 19 in the other anchor implant 2 until the desired suture tension for drawing together the two pieces of tissue 20 and 21 is reached. Once this is the case, the guide wire 4 can also be pulled out of the second anchor implant 2, with the result that the suture 19 also slides into the clamping section 11 in the second anchor implant 2 and is clamped there (FIG. 6). Thus, both anchor implants 2 are joined together with the desired suture length and hence also with the desired tension for joining the pieces of tissue 20 and 21 without any formation of knots.

Still further anchor implants 2 may also be lined up in the same way on the same suture 19. Thus, quite a large number of anchor implants 2 can be joined together under tension in the described manner with the same suture. After installing the first anchor implant 2, this is simply achievable by successively installing further anchor implants 2, by tightening the suture in the installed anchor implants 2, by withdrawing the guide instrument with the guide wire 4 and by thereby also securing the suture in the newly installed anchor implant 2. This is a very simple procedure which can be carried out quickly. In particular, the time required for making a knot is eliminated, and, in addition, complicated handling of the suture ends, which can cause great difficulties, in particular, in endoscopic operations, is thereby rendered superfluous.

What is claimed is:

1. Suture anchor system for joining pieces of tissue comprising at least two arrow-shaped or pin-shaped anchor implants joined to one another by a flexible suture fastened to the anchor implants, wherein at least one of the anchor implants has a continuous longitudinal passageway having a longitudinally displaceable core and a suture guide for receiving a suture common to all anchor implants for longitudinal displacement in the suture guide, a clamping device for securing the suture in the suture guide is associated with the suture guide, and the clamping device is inactive so long as the core is located inside the longitudinal passageway and only becomes active when the core is pulled out of the longitudinal passageway.

2. Suture anchor system in accordance with claim 1, wherein a first anchor implant is securely fastened to the suture and all other anchor implants have a longitudinal passageway with a removable core and a suture guide with a clamping device.

3. Suture anchor system in accordance with claim 2, wherein the first anchor implant also has a continuous longitudinal passageway.

4. Suture anchor system in accordance with claim 1, wherein all anchor implants have a longitudinal passageway with a removable core and a suture guide with a clamping device.

5. Suture anchor system in accordance with claim 4, wherein the suture carries a stop member at its end.

6. Suture anchor system in accordance with claim 1, wherein the anchor implants carry barbs on their exterior surface.

7. Suture anchor system in accordance with claim 1, wherein the anchor implant and/or the suture consist of absorbable plastic material.

8. Suture anchor system in accordance with claim 1, wherein the suture guide has a clamping section extending through the longitudinal passageway and a displacement section disposed adjacent the longitudinal passageway, the core inserted in the anchor implant blocks off the clamping section from the displacement section, and the clamping device is disposed in the clamping section.

9. Suture anchor system in accordance with claim 8, wherein the clamping device is a slot which tapers towards the bottom thereof, and into which the suture is placed and clamped between the side walls thereof when the suture is displaced towards the bottom of the slot.

10. Suture anchor system in accordance with claim 9, wherein guides for the suture which are bent at an angle towards the bottom of the slot adjoin the slot on both sides thereof.

11. Suture anchor system in accordance with claim 10, wherein the guides for the suture are in the form of channels open or closed at the sides, which extend at both sides of the longitudinal passageway substantially parallel thereto in the anchor implant and at one end open into the bottom of the slot.

12. Suture anchor system in accordance with claim 9, wherein the slot extends diametrically through the anchor implant.

13. Suture anchor system in accordance with claim 9, wherein the side walls of the slot converge at an acute angle towards the bottom thereof.

14. Suture anchor system in accordance with claim 13, wherein the side walls have a concave curvature in cross section.

15. Suture anchor system in accordance with claim 9, wherein the slot continues at its end opposite the bottom thereof into the displacement section disposed outside the longitudinal passageway and forming part of the slot, and the side walls of the slot in the displacement section are spaced at a distance from one another which is greater than the diameter of the suture.

16. Suture anchor system in accordance with claim 15, wherein the plane of the slot in the displacement section is bent at an angle in relation to the plane of the slot in the clamping section.

17. Suture anchor system in accordance with claim 16, wherein the plane of the slot in the displacement section is bent in relation to the plane of the slot in the clamping section at an angle of between 30° and 90°.

18. Suture anchor system in accordance with claim 16, wherein the slot is curved in the area of transition between the clamping section and the displacement section.

19. Suture anchor system in accordance with claim 15, wherein the slot at the outer end of the displacement section is open towards the outside at the circumferential surface of the anchor implant.

20. Suture anchor system in accordance with claim 1, wherein the core is a guide wire.

* * * * *